(12) United States Patent
Hall et al.

(10) Patent No.: US 8,999,644 B2
(45) Date of Patent: Apr. 7, 2015

(54) METHOD FOR DETECTING THE PRESENCE OF A DNA MINOR CONTRIBUTOR IN A DNA MIXTURE

(75) Inventors: Diana Hall, Lausanne (CH); Vincent Castella, Le Mont-sur-Lausanne (CH)

(73) Assignee: Centre Hospitalier Universitaire Vaudois, Lausanne (CH)

( * ) Notice: Subject to any disclaimer, the term of this patent is extended or adjusted under 35 U.S.C. 154(b) by 6 days.

(21) Appl. No.: 13/883,314

(22) PCT Filed: Nov. 4, 2011

(86) PCT No.: PCT/IB2011/054919
§ 371 (c)(1),
(2), (4) Date: May 3, 2013

(87) PCT Pub. No.: WO2012/059888
PCT Pub. Date: May 10, 2012

(65) Prior Publication Data
US 2013/0260380 A1    Oct. 3, 2013

(30) Foreign Application Priority Data

Nov. 5, 2010 (CH) ..................................... 1859/10
Apr. 14, 2011 (CH) ..................................... 0660/11

(51) Int. Cl.
C12Q 1/68    (2006.01)
C12P 19/34    (2006.01)

(52) U.S. Cl.
CPC ............ C12Q 1/6827 (2013.01); C12Q 1/6848 (2013.01); C12Q 1/6858 (2013.01); C12Q 1/6888 (2013.01); C12Q 1/686 (2013.01)

(58) Field of Classification Search
CPC ..... C12Q 1/686; C12Q 1/6827; C12Q 1/6858
See application file for complete search history.

(56) References Cited

U.S. PATENT DOCUMENTS

2004/0197797 A1* 10/2004 Inoko et al. ...................... 435/6
2011/0143347 A1* 6/2011 Bohme et al. ................. 435/6.11

FOREIGN PATENT DOCUMENTS

WO    WO 2007/100911    9/2007    ............... C12Q 1/68

OTHER PUBLICATIONS

Inoko et al. Method for analysing genome using microsatellite genetic polymorphism markers. GenBank Accession No. DJ472015, (2008).*
Clayton, T. M., et al. (1998) "Analysis and interpretation of mixed forensic stains using DNA STR profiling", Forensic Science International, 91(1): 55-70.
Hall, D., et al. (2011) "DIP-STR: a new marker for resolving unbalanced DNA mixtures", Forensic Science International: Genetics Supplement Series, 3(1): E1-E2.
Hering, S., et al. (2008) "Complex variability of intron 40 of the von Willebrand factor ( vWF) gene", International Journal of Legal Medicine, 122(1): 67-71.
Homer, N., et al. (2008) "Resolving individuals contributing trace amounts of DNA to highly complex mixtures using high-density SNP genotyping Microarrays", PLOS Genetics, 4(8): e1000167
Watanabe, G., et al. (1998) "Simultaneous determination of STR polymorphism and a new nucleotide substitution in its flanking region at the CD4 locus", Journal of Forensic Sciences, 43(4): 733-737.
International Search Report dated Mar. 9, 2012 issued in PCT Application No. PCT/IB2011/054919.

* cited by examiner

Primary Examiner — Teresa E Strzelecka
Assistant Examiner — David Thomas
(74) Attorney, Agent, or Firm — Harness, Dickey & Pierce, P.L.C.

(57) ABSTRACT

The present invention concerns a method of detecting the presence of a DNA minor contributor in a DNA mixture by determining several haplotypes present in said one or more DNA samples.

24 Claims, 2 Drawing Sheets

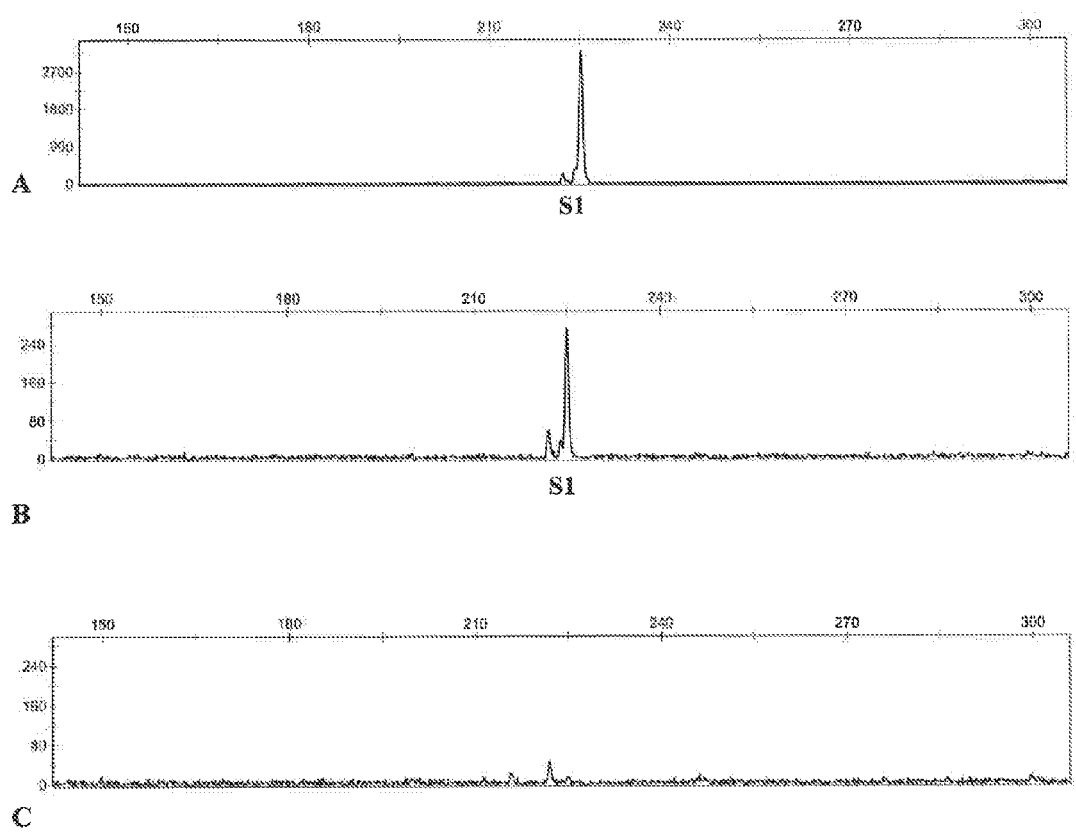

SEQUENCE LISTING

<160> NUMBER OF SEQ ID NOS: 18

<210> SEQ ID NO 1
<211> LENGTH: 23
<212> TYPE: DNA
<213> ORGANISM: Homo sapiens

<400> SEQUENCE: 1
aaaagtgtgt cagatcattt gaa                                              23

<210> SEQ ID NO 2
<211> LENGTH: 20
<212> TYPE: DNA
<213> ORGANISM: Homo sapiens

<400> SEQUENCE: 2
atccttctgg aaagatgctt                                                  20

<210> SEQ ID NO 3
<211> LENGTH: 25
<212> TYPE: DNA
<213> ORGANISM: Homo sapiens

<400> SEQUENCE: 3
tcatgagcta aatattactc agtgc                                            25

<210> SEQ ID NO 4
<211> LENGTH: 25
<212> TYPE: DNA
<213> ORGANISM: Homo sapiens

<400> SEQUENCE: 4
cttatagctt ttttcaaatg atctg                                            25

<210> SEQ ID NO 5
<211> LENGTH: 26
<212> TYPE: DNA
<213> ORGANISM: Homo sapiens

<400> SEQUENCE: 5
aaagatgctt tatatttcca gttatt                                           26

<210> SEQ ID NO 6
<211> LENGTH: 26
<212> TYPE: DNA
<213> ORGANISM: Homo sapiens

<400> SEQUENCE: 6
aaagatgctt tatatttcca gtttag                                           26

<210> SEQ ID NO 7
<211> LENGTH: 23
<212> TYPE: DNA
<213> ORGANISM: Homo sapiens

<400> SEQUENCE: 7
ctgaagctaa gaaatgctaa aaa                                              23

<210> SEQ ID NO 8
<211> LENGTH: 20
<212> TYPE: DNA
<213> ORGANISM: Homo sapiens

<400> SEQUENCE: 8

```
ggcaccttag tgatatgtgg                                              20
```

```
<210> SEQ ID NO 9
<211> LENGTH: 24
<212> TYPE: DNA
<213> ORGANISM: Homo sapiens

<400> SEQUENCE: 9
catgtttgtc acctagtaaa gacc                                         24
```

```
<210> SEQ ID NO 10
<211> LENGTH: 20
<212> TYPE: DNA
<213> ORGANISM: Homo sapiens

<400> SEQUENCE: 10
atgaaatgta cctgcctttg                                              20
```

```
<210> SEQ ID NO 11
<211> LENGTH: 26
<212> TYPE: DNA
<213> ORGANISM: Homo sapiens

<400> SEQUENCE: 11
tttactacta ggaggctctc tttgtt                                       26
```

```
<210> SEQ ID NO 12
<211> LENGTH: 26
<212> TYPE: DNA
<213> ORGANISM: Homo sapiens

<400> SEQUENCE: 12
tttactacta ggaggctctc ttcatc                                       26
```

```
<210> SEQ ID NO 13
<211> LENGTH: 20
<212> TYPE: DNA
<213> ORGANISM: Homo sapiens

<400> SEQUENCE: 13
caggatctca tgcaggatac                                              20
```

```
<210> SEQ ID NO 14
<211> LENGTH: 20
<212> TYPE: DNA
<213> ORGANISM: Homo sapiens

<400> SEQUENCE: 14
tgttgtttag cttcctggac                                              20
```

```
<210> SEQ ID NO 15
<211> LENGTH: 20
<212> TYPE: DNA
<213> ORGANISM: Homo sapiens

<400> SEQUENCE: 15
aaagtgagga gtcaaggagg                                              20
```

```
<210> SEQ ID NO 16
<211> LENGTH: 25
<212> TYPE: DNA
<213> ORGANISM: Homo sapiens
```

```
<400> SEQUENCE: 16
gaatctgaag gtgttctaaa agtaa                                              25

<210> SEQ ID NO 17
<211> LENGTH: 20
<212> TYPE: DNA
<213> ORGANISM: Homo sapiens

<400> SEQUENCE: 17
ggtctgtcat tacccactgg                                                    20

<210> SEQ ID NO 18
<211> LENGTH: 22
<212> TYPE: DNA
<213> ORGANISM: Homo sapiens

<400> SEQUENCE: 18
ggtctgtcat tacccagtat tc                                                 22
```

METHOD FOR DETECTING THE PRESENCE OF A DNA MINOR CONTRIBUTOR IN A DNA MIXTURE

PRIORITY STATEMENT

This application is a national stage application under 35 U.S.C. §371 of PCT International Application No. PCT/IB2011/054919 which has an International filing date of 4 Nov. 2011, and which claims the benefit under 35 U.S.C. §119 to Switzerland Application No. 01859/10 filed 5 Nov. 2010 and Switzerland Application No. 00660/11 filed 14 Apr. 2011. The contents of each application recited above are incorporated herein by reference in their entirety.

FIELD OF THE INVENTION

The present invention concerns a method of detecting the presence of a DNA minor contributor in a DNA mixture by determining several haplotypes present in said one or more DNA samples.

BACKGROUND OF THE INVENTION

Microsatellites, or STRs, represent the most discriminating genetic marker used in forensic genetics to identify traces and persons. They are helpful to analyze samples containing the DNA of one person or the DNA of two persons occurring in comparable quantities. This is why those genetic markers have been retained to feed national DNA databases used to fight against criminals all around the world. For instance, the Swiss DNA database, launched in 2000, contains presently more than 140,000 DNA profiles. One limitation of STRs is that they cannot resolve unbalanced mixtures. In particular, the minor contributor of a DNA mixture cannot be detected using conventional DNA markers (STR, SNP, Sanger sequencing, etc.) when it represents less than about 10% of the major contributor. Below this threshold, the DNA profile of the minor contributor, who is potentially the perpetrator of the crime, can be masked, preventing his genetic identification.

Such situation is frequent and may happens for instance when analyzing touched object (e.g. samples from the steering-wheel of a stolen cars, screw-drivers, door handles, etc) or samples from rape cases (e.g. gynecological swabs). A way to avoid this limitation is to use STRs located on the Y chromosome. Those sex-specific markers can detect a few male DNA within a high background of female DNA. However, Y-STRs are of limited information mainly for three reasons. First, they are helpful to analyze only mixtures of male and female DNA when the male is the minor contributor and not other types of mixtures. Second, they do not discriminate among paternally related males and therefore allow to identify a lineage. Third, some Y-markers are frequent in the population compromising the discrimination of different male lineages and reducing the power of the DNA evidence.

In view of the above, there is a need to develop an improved method to overcome the identified limits and enabling to identify an individual, rather than a lineage.

SUMMARY OF THE INVENTION

The present invention concerns a method of detecting the presence of a DNA minor contributor in a DNA mixture by determining several haplotypes present in said one or more DNA samples, each haplotype containing a short tandem repeat (STR) locus and a deletion insertion polymorphism (DIP) locus. According to one embodiment, the method comprises:

i) determining the DIP genotype of the major DNA contributor in order to select suitable DIP primers for a specific amplification of the minor DNA contributor, ii) contacting said at least one or more DNA samples to be analyzed with a set of primers selected from the group comprising a primer specific to the STR locus, a primer overlapping the short allele of the DIP locus (S-DIP), a primer overlapping the long allele of the DIP locus (L-DIP), or a combination of two or more of these primers, iii) amplifying the DNA mixture, for each DIP-STR locus, with the L-DIP primer and the STR primer when the major contributor is SS, or with the S-DIP primer and the STR primer when the major contributor is LL, wherein resulting amplicons, when present, correspond to the DIP-STR haplotype of the minor contributor, iv) evaluating the amplified amplicons in the DNA mixture to determine the haplotypes present at each of the loci analyzed in the set within the minor contributor and evaluating the match with the samples collected for comparison.

Additionally, the present invention also envisioned a kit for practicing one or more of the above described methods and optionally with reagents, primers and/or probes as well as instructions for use.

DESCRIPTION OF THE FIGURES

FIG. 2: Detection of fetal DNA by DIP-STR amplification of maternal plasma. (A) Paternal DIP-STR haplotype S1. (B) DIP-STR analysis of the plasma of the mother at 30 weeks of pregnancy. The fetal haplotype S1, transmitted from the father can be detected. (C) DIP-STR analysis of DNA from the saliva of the mother. This sample doesn't amplify the DIP-STR haplotype S1 observed in the plasma, confirming the paternal transmission of the haplotype detected in B.

DETAILED DESCRIPTION OF THE INVENTION

Figure 1:
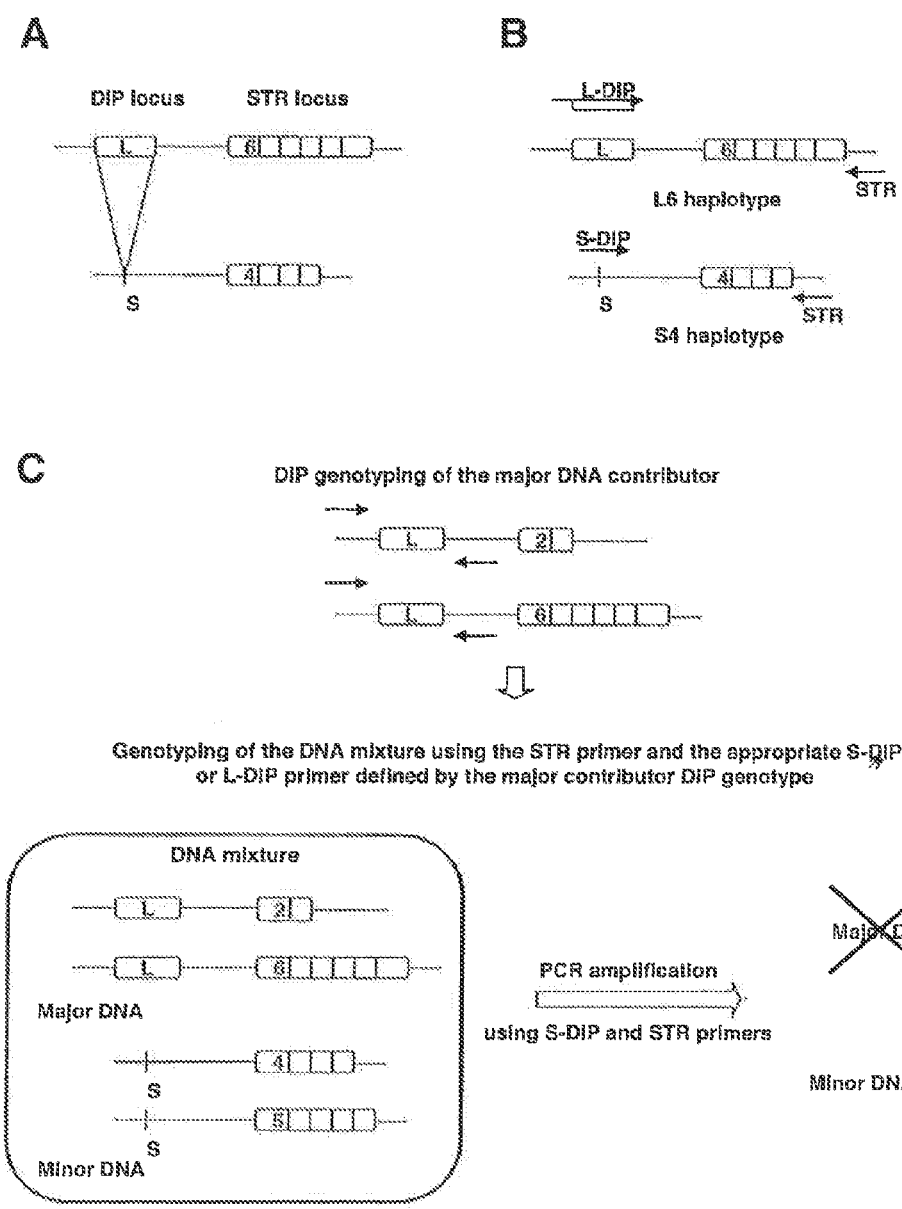
FIG. 1 (A): Structure of a DIP-STR locus. A DIP polymorphism is linked to a STR polymorphism. (B) Allele specific PCR is realized by using two sets of primers: the L-DIP primer which carries the inserted sequence specific to the long allele and the S-DIP primer which is specific to the short allele due to the absence of the inserted sequence. In both cases the STR primer located downstream the STR polymorphism allows the amplification of the complete DIP-STR locus. (C) Standard casework procedure for the analysis of a mixture of two DNAs. First the DIP genotype of the major DNA contributor is determined. Second the DNA mixture is genotyped using the L-DIP and STR primers when the major contributor is SS, or using the S-DIP and STR primers when the major contributor is LL. This procedure repeated for a panel of DIP-STR locus generates the DIP-STR profile of the minor contributor.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. Additionally, the term "comprising" also encompasses the term "consisting".

As used in the specification and claims, the singular form "a", "an" and "the" include plural references unless the context clearly dictates otherwise.

As used herein, "at least one" means "one or more."

A "DNA mixture" is formed by DNA samples from more than one source. Usually, a DNA mixture is formed from samples arising from the given person which constitute the "DNA major contributor" and from a first other person ("DNA minor contributor").

A "deletion insertion polymorphism (DIP) locus" is a length multiallelic polymorphism created by deletions or insertions of one or more nucleotides in the genome, Weber et al. (2002) "Human diallelic insertion/deletion polymorphism. Am J Hum Genet, 71, 854-852. DIPs may be selected among the following non limiting examples: MID1950 which is a diallelic DIP polymorphism (−/AAT) located on chromosome 20p13 (UCSC position build May 1, 2004, 3413383), MID1107 which is a diallelic DIP polymorphism (−/TGTT) located on chromosome 5p15.33 (UCSC position build May 1, 2004, 3450118) and MID1013 which is a DIP diallelic polymorphism (−/CCAG) located on chromosome 5q23.2 (UCSC position build May 1, 2004, 126870901).

As used herein, a "haplotype" refers to a set of closely linked genetic markers present on one chromosome which tend to be inherited together (i.e. not easily separable by recombination). In the present case, a haplotype comprises a STR and a DIP and may be selected among the following non limiting examples: MID1950-D20S473, MID1107-D5S1980 and MID1013-D5S490.

As used herein, "amplicons" are fragments of DNA formed as the products of natural or artificial amplification events. For example, they can be formed via polymerase chain reactions (PCR) or ligase chain reactions (LCR), as well as by natural gene duplication.

An "allele", as used herein, refers to one specific form of a genetic sequence or a single nucleotide position within a genetic sequence (such as a gene) within a cell, an individual or within a population, the specific form differing from other forms of the same gene in the sequence of at least one, and frequently more than one, variant sites within the sequence of the gene. The sequence may or may not be within a gene. The sequences at these variant sites that differ between different alleles are termed "variances", "polymorphisms", or "mutations". At each autosomal specific chromosomal location or "locus", an individual possesses two alleles, one inherited from one parent and one from the other parent, for example one from the mother and one from the father.

A "short tandem repeat" or "STR" is a section of DNA which contains a number of repetitions of a certain short sequence. In human DNA, each person might have a different number of repetitions at any given STR site. STRs may be selected among the following non limiting examples: D20S473, D5S1980 and D5S490.

As used herein, a "locus (or genetic locus)" refers to a specific position on a chromosome. Alleles of a locus are located at identical sites on homologous chromosomes.

A "primer" means a single-stranded oligonucleotide or DNA fragment which hybridizes with opposing strands of a locus. DNA amplification requires two primers including, primer 1 that hybridizes to a single strand at one end of the DNA sequence to be amplified and primer 2 that hybridizes with the other end on the complementary strand of the DNA sequence to be amplified. Primer length is usually between 18-30 nt.

A "primer specific to a locus" refers to a primer that specifically hybridizes with a portion of the stated locus or its complementary strand, at least for one allele of the locus, and does not hybridize efficiently with other DNA sequences under the conditions used in the amplification method.

Non limiting examples of primers are selected from the following groups:

Haplotype MID1950-D20S473

```
DIP primers:
MID1950-Fw 5FAM
                                    (SEQ ID No: 1)
5'AAA AGT GTG TCA GAT CAT TTG AA3'

MID1950-Rev
                                    (SEQ ID No: 2)
5'ATC CTT CTG GAA AGA TGC TT3'

STR primers:
D20S473-Fw NED
                                    (SEQ ID No: 3)
5'TCA TGA GCT AAA TAT TAC TCA GTG C3'

D20S473-Rev
                                    (SEQ ID No: 4)
5'CTT ATA GCT TTT TTC AAA TGA TCT G3'

L-DIP and S-DIP primers:
L-MID1950-Rev
                                    (SEQ ID No: 5)
5'AAA GAT GCT TTA TAT TTC CAG TTA TT3'

S-MID1950-Rev
                                    (SEQ ID No: 6)
5'AAA GAT GCT TTA TAT TTC CAG TTT AG3'
```

Haplotype MID1107-D5S1980

```
DIP primers:
MID1107-Fw VIC
                                    (SEQ ID No: 7)
5'CTG AAG CTA AGA AAT GCT AAA AA3'

MID1107-Rev
                                    (SEQ ID No: 8)
5'GGC ACC TTA GTG ATA TGT GG3'

STR primers:
D5S1980-Fw NED
                                    (SEQ ID No: 9)
5'CAT GTT TGT CAC CTA GTA AAG ACC3'

D5S1980-Rev
                                    (SEQ ID No: 10)
5'ATG AAA TGT ACC TGC CTT TG3'

L-DIP and S-DIP primers:
L-MID1107-Rev
                                    (SEQ ID No: 11)
5'TTT ACT ACT AGG AGG CTC TCT TTG TT3'

S-MID1107-Rev
                                    (SEQ ID No: 12)
5'TTT ACT ACT AGG AGG CTC TCT TCA TC3'
```

MID1013-D5S490

```
DIP primers:
MID1013-Fw NED
                                        (SEQ ID No: 13)
5'CAG GAT CTC ATG CAG GAT AC3'

MID1013-Rev
                                        (SEQ ID No: 14)
5'TGT TGT TTA GCT TCC TGG AC3'

STR primers:
D5S490-Fw VIC
                                        (SEQ ID No: 15)
5'AAA GTG AGG AGT CAA GGA GG3'

D5S490-Rev
                                        (SEQ ID No: 16)
5'GAA TCT GAA GGT GTT CTA AAA GTA A3'

L-DIP and S-DIP primers:
L-MID1013-Fw 5FAM
                                        (SEQ ID No: 17)
5'GGT CTG TCA TTA CCC ACT GG3'

S-MID1013-Fw 5FAM
                                        (SEQ ID No: 18)
5'GGT CTG TCA TTA CCC AGT ATT C3'
```

A "DNA blocking primer" refers to a primer that binds to a specific DNA by preference and modified so that it does not prime amplification. Application of blocking oligonucleotides to improve signal-to-noise ratio in a PCR. Vestheim H, Deagle B E, Jarman S N. Methods Mol Biol. 2011; 687:265-74. Blocking primers to enhance PCR amplification of rare sequences in mixed samples—a case study on prey DNA in Antarctic krill stomachs. Vestheim H, Jarman S N. Front Zool. 2008 Jul. 20; 5:12. Promising nucleic acid analogs and mimics: characteristic features and applications of PNA, LNA, and morpholino. Karkare S, Bhatnagar D. Appl Microbiol Biotechnol. 2006 August; 71(5):575-86. Epub 2006 May 9. Review Non limiting examples of DNA blocking primers are selected from the following groups:

```
L-DIP and S-DIP blocking primers:
L-MID1950-Rev
                                        (SEQ ID No: xxx)
5'AAA GAT GCT TTA TAT TTC CAG TTA TT 3'C3

S-MID1950-Rev
                                        (SEQ ID No: xxxx)
5'AAA GAT GCT TTA TAT TTC CAG TTT AG 3'C3

L-MID1107-Rev
                                        (SEQ ID No: xxx)
5'TTT ACT ACT AGG AGG CTC TCT TTG TT 3'C3

S-MID1107-Rev
                                        (SEQ ID No: xxx)
5'TTT ACT ACT AGG AGG CTC TCT TCA TC 3'C3

L-MID1013-Fw 5FAM
                                        (SEQ ID No: xxx)
5'GGT CTG TCA TTA CCC ACT GG 3'C3

S-MID1013-Fw 5FAM
                                        (SEQ ID No: xxx)
5'GGT CTG TCA TTA CCC AGT ATT C 3'C3
```

C3 at the 3'-end of the primer sequence indicate the C3spacer (3 hydrocarbons) CPG, a standard primer modification to make blocking primers.

The addition of a C3 spacer (3 hydrocarbons) to the 3"-end of an oligonucleotide can prevent e.g. its elongation during a PCR without influencing its annealing properties in any meaningful way. Such a modification is therefore well suited for hybridization probes used in a PCR reaction.

Because of competition for primers during PCR amplification, the minor contributor of a two-person's DNA mixture cannot be detected using conventional DNA markers (STR, SNP, Sanger sequencing, etc.) when it represents less than about 10% of the major contributor. In order to allow going beyond this limit, the Applicants have developed a method of detecting the presence of a DNA minor contributor in a DNA mixture by determining several haplotypes present in said one or more DNA samples, each haplotype containing a short tandem repeat (STR) locus and a deletion insertion polymorphism (DIP) locus.

In one embodiment, the method of the invention comprises the following steps:

i) determining the DIP genotype of the major DNA contributor in order to select suitable DIP-STR primers for a specific amplification of the minor DNA contributor, ii) contacting said at least one or more DNA samples to be analyzed with a set of primers selected from the group comprising a primer specific to the STR locus, a primer overlapping the short allele of the DIP locus (S-DIP), a primer overlapping the long allele of the DIP locus (L-DIP), or a combination of two or more of these primers, iii) amplifying the DNA mixture, for each DIP-STR locus, with the L-DIP and STR primers when the major contributor is SS, or with the S-DIP and STR primers when the major contributor is LL, wherein resulting amplicons, when present, correspond to the DIP-STR haplotype of the minor contributor, iv) evaluating the amplified amplicons in the DNA mixture to determine the haplotypes present at each of the loci analyzed in the set within the minor contributor and evaluating the match with the samples collected for comparison.

Mixtures of DNA can be prepared for use in the method of this invention using any method of DNA preparation which is compatible with the amplification technique. Many such methods are suitable for use in preparing genomic DNA samples for use in the method of this invention, including, but not limited to, the methods of DNA sample preparation described by Castella et al. (2006) "Forensic evaluation of the QIAshredder/QIAamp DNA extraction procedure," Forensic Sci Int 156: 70-73.

Optionally, DNA concentrations can be measured prior to use in the method of the present invention, using any standard method of DNA detection. However, the DNA concentration is preferably measured by quantitative real-time PCR (qRT-PCR) as first described by Green et al., (2005) "Developmental validation of the quantifiler real-time PCR kits for the quantification of human nuclear DNA samples" J Forensic Sci. 50:809-825.

Step i)

Preferably, the determination of the DIP genotype of the major DNA contributor in step i) comprises contacting said one or more DNA samples or the DNA of the major contributor with primers which bind at each side of the DIP locus.

Usually, the DIP primers are not allele specific. They are located at each side of the DIP locus, without specific requirement. This typing may be done either on a sample containing only the DNA of the major contributor (e.g. a reference sample), or directly on the one or more DNA samples (at this stage only the major contributor's DIP-alleles matter).

This step further comprises amplifying the DIP locus and evaluating the amplicons. DIP primers may be multiplexed in order to amplify several loci in one PCR reaction.

The resulting amplicons can then be separated and detected with any other suitable technique. Gel electrophoresis, capillary electrophoresis and MALDI-TOF Mass Spectrometry. Electrophoresis is also preferably used to separate the products of the multiplex amplification reaction, more preferably denaturing polyacrylamide gel electrophoresis (see, e.g., Sambrook, J. et al. (1989) In Molecular Cloning-A Laboratory Manual, 2nd edition, Cold Spring Harbor Laboratory Press, pp. 13.45-13.57). Separation of DNA fragments in a denaturing polyacrylamide gel occurs based on fragment size.

A Genetic Analyzer is preferred for detecting capillary electrophoresis based DNA analysis of multi-color fluorescence-amplicons (Applied Biosystems, Foster City, Calif., USA).

Once the amplified alleles are separated by capillary electrophoresis of fluorescently labeled amplicons (Applied Biosystems, Foster City, Calif., USA).

The alleles present in the DNA sample are preferably determined by comparison to a size standard such as a DNA marker or a locus-specific allelic ladder to determine the alleles present at each locus within the sample. The most preferred size marker for evaluation of a multiplex amplification containing two or more polymorphic loci consists of a combination of allelic ladders for each of the loci being evaluated. See, e.g., description of allelic ladders and method of ladder construction in Schumm et al., supra, at p. 178.

The preferred size marker for evaluation of a multiplex amplification containing two or more polymorphic loci which are generated using fluorescently-labeled primers for each locus consists of a combination of fluorescently-labeled allelic ladders for the loci being evaluated. Following the construction of allelic ladders for individual loci, they may be mixed and loaded for electrophoresis at the same time as the loading of amplified samples occurs. Each allelic ladder co-migrates with alleles in the sample from the corresponding locus. A permanent record of the data can be generated using Automatic Processor Compatible (APC) film (STR systems manual #TMD004, available from Promega Corporation, Madison, Wis.) or with use of a fluorescent detection instrument (STR systems manual #TMD006, also available from Promega Corporation, Madison, Wis.).

This step i) allows to determine, at each locus, if the major contributor of the DNA mixture is homozygous for the deletion (SS), homozygous for the insertion (LL), or heterozygous for both (SL).

Since biological samples may contain degraded DNA, it is important to select DIP and STR loci that are as close as possible in order to allow the amplification of compromised DNA. Consequently, the STR and the DIP alleles are linked and constitute a haplotype. Preferably, the distance between the STR locus and the DIP locus is smaller than 1000 base pairs, most preferably smaller than 800 base pairs, and even more preferably smaller than 500 bases pairs.

Step ii)

Step ii) of the method of the invention further comprises contacting said at least one or more DNA samples to be analyzed with a set of primers selected from the group comprising a primer specific to the STR locus, a primer overlapping the short allele of the DIP locus (S-DIP), a primer overlapping the long allele of the DIP locus (L-DIP), or a combination of two or more of these primers.

The S-DIP and L-DIP primers are allele specific. The typing of the minor contributor requires the use of the opposite S-DIP or L-DIP primer compared to the major contributor's DIP alleles: e.g. the S-DIP and STR primers are used when the major contributor has the LL DIP alleles, whereas the L-DIP and STR primers are used when the major contributor has the SS DIP alleles.

In Step iii) of the present invention, the DNA mixture is amplified, for each DIP-STR locus, with the L-DIP and STR primers when the major contributor is SS, or with the S-DIP and STR primers when the major contributor is LL, wherein resulting amplicons, when present, correspond to the DIP-STR haplotype of the minor contributor.

In both situations, the second primer, located next to the STR locus, is the same. Resulting amplicons can be separated and detected, for example, with a capillary electrophoresis. Note that the major contributor's DIP loci that are heterozygous (SL) should be dropped since the DNA of the major contributor will hide in any case the minor one. For each DIP-STR locus, this step allows to determine the haplotype(s) characterizing the minor contributor. Typical results for the minor contributor of the DNA mixture are:

Two DIP-STR haplotypes are detected, for instance S14 and S17 (or L14 and L17, depending on the specific DIP-STR primer used). The minor contributor is homozygous at the DIP locus and heterozygous at the STR locus (e.g. S14-S17).

One DIP-STR haplotype is detected, for instance S14 (or L14, depending on the specific DIP-STR primer used). This means that the minor contributor is either homozygous at the DIP and STR loci (e.g. S14-S14), or that the minor contributor is heterozygous at the DIP locus and heterozygous at the STR locus (e.g. S14-L17), or that the minor contributor is heterozygous at the DIP locus and homozygous at the STR locus (e.g. S14-L14).

No DIP-STR haplotype is detected. This means that the minor contributor is homozygous for the same DIP alleles than the major contributor. No information is therefore available. An alternative explanation could be that the minor contributor is too diluted or absent. This is why several DIP-STR loci have to be typed for each sample.

Amplification methods include, but are not limited to, PCR including real time PCR (RT-PCR), strand displacement amplification, strand displacement amplification using Phi29 DNA polymerase (U.S. Pat. No. 5,001,050), transcription-based amplification, self-sustained sequence replication ("3SR"), the Q.beta. replicase system, nucleic acid sequence-based amplification ("NASBA"), the repair chain reaction ("RCR"), and boomerang DNA amplification (or "BDA"). PCR is the preferred method of amplifying the DNA mixture.

PCR may be carried out in accordance with techniques known by the skilled artisan. In general, PCR involves, first, treating a nucleic acid sample (e.g., in the presence of a heat stable DNA polymerase) with a pair of amplification primers. One primer of the pair hybridizes to one strand of a target polynucleotide sequence. The second primer of the pair hybridizes to the other, complementary strand of the target polynucleotide sequence. The primers are hybridized to their target polynucleotide sequence strands under conditions such that an extension product of each primer is synthesized which is complementary to each nucleic acid strand. The extension product synthesized from each primer, when it is separated from its complement, can serve as a template for synthesis of the extension product of the other primer. After primer extension, the sample is treated to denaturing conditions to separate the primer extension products from their templates. These steps are cyclically repeated until the desired degree of amplification is obtained.

Step iv)

The amplified amplicons in the DNA mixture are then evaluated in order to determine the haplotypes present at each of the loci analyzed in the set within the minor contributor. Compare the minor contributor DIP-STR haplotypes with those of comparison samples analyzed with the same specific S-DIP or L-DIP and STR primers. Statistical evaluation is possible using DIP-STR haplotype frequencies from a reference population.

Preferably, the one or more DNA sample to be analyzed, which may be present in the DNA mixture, is isolated from biological material, wherein the biological material can be selected from the group comprising soft and hard tissues, blood, semen, epithelial or vaginal cells, hair, saliva, urine, feces, amniotic fluid containing placental cells or fetal cells, and mixtures of any of the tissues listed above.

Preferably also, primers capable of binding to a region flanking each of the loci in the set are used in co-amplifying the loci, wherein at least one of the primers used in co-amplifying each locus has a dye or fluorescent label covalently attached thereto such that the amplified alleles produced therefrom are fluorescently labeled, and wherein the separated alleles in the polyacrylamide gel are determined by visualizing the alleles with fluorescent analysis. Examples of fluorescent label include Red Labels (5-carboxytetramethylrhodamine [5TMR]; 5.6-carboxytetramethylrhodamine [5(6)TMR]; 6-carboxytetramethylrhodamine [6TMR]; Lissamine Rhodamine B [LRhodB]), Green Labels (5-carboxyfluoresceine [5FAM]; 5,6-carboxyfluoresceine [5(6)FAM]; 6-carboxyfluoresceine [6-FAM]; Methoxy coumarin acetic acid) and Other Fluorescence Labeled Peptide probes such as FITC/5-FAM (N-Terminal, Y/N Ahx), MCA (N-Terminal), HYNIC (N-Terminal), DTPA (N-Terminal, Texas Red, Bodipy; Aminocoumarin, TET™, VIC™, HEX™, LIZ™, NED™ or PET™ dyes and many others.

In a second alternative, the method of the invention comprises the following steps:

i) contacting at least one or more DNA mixtures and/or DNA samples to be analyzed with a combination of two or more sets of primers selected from the group comprising a primer specific to the STR locus, a primer overlapping the short allele of the DIP locus (S-DIP), and a primer overlapping the long allele of the DIP locus (L-DIP), ii) amplifying said at least one or more DNA mixtures and/or DNA samples, wherein resulting amplicons, when present, correspond to the DIP-STR haplotypes of the minor contributor, and of the major contributor, iii) evaluating the amplified amplicons in the DNA mixture and/or DNA sample to determine the haplotypes present at each of the loci analyzed in said at least one or more DNA mixtures and/or DNA samples and evaluating the match between said at least two or more DNA mixtures and/or DNA samples for comparison.

In step iii) of this second alternative, the DIP-STR haplotypes of the major and minor contributors are identified by either reference DNA samples substraction or by electropherogram peak height or area analysis. More precisely, the difference of peak height or area between the major and the minor contributors of the DNA mixture is directly related to the proportion of DNA from each contributor. Therefore, the peaks corresponding to the DIP-STR haplotype of the minor contributor can be recognized for their smaller size when compared to those of the major contributor.

In a third alternative of the invention, the method comprises the following steps:

i) determining the DIP genotype of the major DNA contributor in order to select suitable DIP primers for a specific amplification of the minor DNA contributor, ii) contacting at least one or more DNA samples to be analyzed with a set of primers selected from the group comprising a primer specific to the STR locus, a primer overlapping the short allele of the DIP locus (S-DIP), a primer overlapping the long allele of the DIP locus (L-DIP), a S-blocking primer, a L-blocking primer or a combination of two or more of these primers, iii) amplifying the DNA mixture, for each DIP-STR locus, with the L-DIP, S-blocking primer and STR primers when the major contributor is SS, or with the S-DIP, L-blocking primer and STR primers when the major contributor is LL, wherein resulting amplicons, when present, correspond to the DIP-STR haplotype of the minor contributor, iv) evaluating the amplified amplicons in the DNA mixture to determine the haplotypes present at each of the loci analyzed in the set within the minor contributor and evaluating the match with the samples collected for comparison.

In step iii) of this third alternative, the use of primers blocking the major DNA contributor in the PCR for amplifying the minor DNA contributor facilitate the selective amplification of the minor DNA contributor and therefore allow its genotyping in the presence of higher amounts of major DNA contributor.

Additionally, the present invention also envisioned a kit for practicing one or more of the above described methods and optionally with reagents, primers and/or probes as well as instructions for use.

Preferably primers and/or probes used for the amplification of PCR amplicons are chosen as described above. Preferably, the primer and/or probe of the invention will be selected from those described supra and from any combinations thereof.

Reagents of interest include reagents for preparing the one or more DNA samples as well as reagents specifically designed for labeling the primers and/or amplifying the loci (DIP or STR). These reagents may be selected from the group comprising dNTPs and/or rNTPs, which may be either premixed or separate, one or more uniquely labeled dNTPs and/or rNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the kits will further include instructions for practicing the methods and arrays described herein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The invention further provides a PCR composition comprising primers and/or probes as described supra and any combinations thereof for use as described.

The invention also concerns the use of the method mentioned herein within the below non limiting contexts:

i) a forensic context when the DNA of two persons is found on a single substrate, for instance when the large amounts of victim's DNA may hide the rapist's DNA on a gynecological swab. Many biological traces analyzed in forensic genetics produce unbalanced DNA mixtures. For instance cases of aggression, homicide and sexual assault traces often contain large amount of the victim's DNA and a small amount of the aggressor's DNA. Besides these three examples, contact stains of various sources can have this feature. All these cases can only be solved with a method that allows detecting the presence of a DNA minor contributor in a DNA mixture, ii) an anti-doping context when small amounts of heterologous blood is transfused to an athlete to improve his performance, iii) after an organ transplant, when small amounts of the donor's DNA may survive in the recipient. Individuals transplanted of heart, liver or kidney may present donor's circulating cells in blood or in urine (kidney transplant). The quantity of donor's DNA is directly correlated to the incidence of acute rejection. This is because both acute and chronic rejection processes are associated with apoptosis of specific cell types within the allograft. Therefore, the present method will have a clinical impact on early noninvasive diagnosis of acute rejection based on DNA mixture analysis of the circulating DNA in the blood of the patient.

iv) within genetic chimera or mosaics and/or v) as prenatal noninvasive paternity testing and prenatal genetic disease diagnosis, after pregnancy when small amounts of the baby's DNA may last in the maternal blood circulation. This DNA is mainly generated by processes of apoptosis and necrosis during placental development. It is therefore a cell-free DNA that can be isolated from the plasma of the mother already at 8 weeks of pregnancy. This fetal DNA represents between 3 to 6% of the total circulating cell-free DNA and therefore it can be analyzed only by using a method that allows detecting the presence of a DNA minor contributor in a DNA mixture. The fetal DNA can be genotyped with a DIP-STR panel for paternity testing (as shown in Example 4 and depicted in FIG. 2) or by using specific DIP-STR markers validated for disease diagnosis. Both analyses allow prenatal screening and diagnosis that are noninvasive and that can be performed already at early pregnancy. These features allow the women to make informed choices about the continuation of the pregnancy or to receive special care for its continuation, if possible.

EXAMPLES

Example 1

MID1950-D20S473

MID1950 is a DIP polymorphism (−/AAT), located on chromosome 20p13 (UCSC position build May 1, 2004, 3413383) at ~190 bp from the STR polymorphism (ATA)n (UCSC position build May 1, 2004 3413570). DIP-STR amplicons are of the size of 215-230 bp. Primers were designed using the PRIMER3 software proposed by Rozen et al. (2000) *Primer3 on the WWW for general users and for biologist programmers*. In: Krawetz S, Misener S (eds) Bioinformatics Methods and Protocols: Methods in Molecular Biology. Humana Press, Totowa, N.J., 365-386.

DIP primers:
MID1950-Fw 5FAM
(SEQ ID No: 1)
5'AAA AGT GTG TCA GAT CAT TTG AA3'

MID1950-Rev
(SEQ ID No: 2)
5'ATC CTT CTG GAA AGA TGC TT3'

STR primers:
D20S473-Fw NED
(SEQ ID No: 3)
5'TCA TGA GCT AAA TAT TAC TCA GTG C3'

D20S473-Rev
(SEQ ID No: 4)
5'CTT ATA GCT TTT TTC AAA TGA TCT G3'

S-DIP and L-DIP primers:
L-MID1950-Rev
(SEQ ID No: 5)
5'AAA GAT GCT TTA TAT TTC CAG TTA TT3'

S-MID1950-Rev
(SEQ ID No: 6)
5'AAA GAT GCT TTA TAT TTC CAG TTT AG3'

Each PCR reaction is performed in a final volume of 20 μL containing 1×PCR buffer (Applied Biosystems) with 1.5 mM $MgCl_2$, 250 μM of each dNTP, 1.2 U AmpliTaq Gold DNA Polymerase, 1 μM of each forward (Fw) and reverse (Rev) primers and 1 ng of genomic DNA. The PCR thermocycling conditions are: 10 min at 95° C.; followed by 60 sec at 94° C., 60 sec at 58° C. and 60 sec at 72° C. for 34 PCR-cycles and a final extension of 30 min at 72° C. The annealing temperature of 58° C. is modified to 52° C. when using DIP-STR primers. The thermal cyclers employed are GeneAmp 9700 (Applied Biosystems). Before capillary electrophoresis, 1 μL PCR product is added to 8.5 μL deionized formamide HI-DI (Applied Biosystems) and 0.5 μL GS-ROX 500 size standard (Applied Biosystems). DNA fragments are separated using an ABI PRISM 3100 Genetic Analyzer (Applied Biosystems) according to manufacturers' instruction and analyzed with GeneMapper ID v3.2 software (Applied Biosystems), with minimum interpretation peak threshold of 50 fluorescent units (RFU).

Example 2

MID1107-D5S1980

MID1107 is a DIP polymorphism (−/TGTT) located on chromosome 5p15.33 (UCSC position build May 1, 2004, 3450118) at ~450 bp from the STR polymorphism D5S1980 (CA)n, (UCSC position build May 1, 2004, 3449670). DIP-STR amplicons are of the size of 662-670 bp.

DIP primers:
MID1107-Fw VIC
(SEQ ID No: 7)
5'CTG AAG CTA AGA AAT GCT AAA AA3'

MID1107-Rev
(SEQ ID No: 8)
5'GGC ACC TTA GTG ATA TGT GG3'

STR primers:
D5S1980-Fw NED
(SEQ ID No: 9)
5'CAT GTT TGT CAC CTA GTA AAG ACC3'

-continued

```
D5S1980-Rev
                                     (SEQ ID No: 10)
5'ATG AAA TGT ACC TGC CTT TG3'

S-DIP and L-DIP primers:
L-MID1107-Rev
                                     (SEQ ID No: 11)
5'TTT ACT ACT AGG AGG CTC TCT TTG TT3'

S-MID1107-Rev
                                     (SEQ ID No: 12)
5'TTT ACT ACT AGG AGG CTC TCT TCATC3'
```

Primer design, PCR reaction and thermocycling (all annealing temperature are 58° C.), capillary electrophoresis and fragment analysis are performed as for example 1, with the use of a longer range size standard GeneScan LIZ 1200 (Applied Biosystems).

Example 3

MID1013-D5S490

MID1013 is a DIP polymorphism (−/CCAG) located on chromosome 5q23.2 (UCSC position build May 1, 2004, 126870901) at ~220 bp from the STR polymorphism D5S490 (CA)n, (UCSC position build May 1, 2004, 126870683). DIP-STR amplicons are of the size of 312-330 bp.

```
DIP primers:
MID1013-Fw NED
                                     (SEQ ID No: 13)
5'CAG GAT CTC ATG CAG GAT AC3'

MID1013-Rev
                                     (SEQ ID No: 14)
5'TGT TGT TTA GCT TCC TGG AC3'

STR primers:
D5S490-Fw VIC
                                     (SEQ ID No: 15)
5'AAA GTG AGG AGT CAA GGA GG3'

D5S490-Rev
                                     (SEQ ID No: 16)
5'GAA TCT GAA GGT GTT CTA AAA GTA A3'

S-DIP and L-DIP primers:
L-MID1013-Fw 5FAM
                                     (SEQ ID No: 17)
5'GGT CTG TCA TTA CCC ACT GG3'

S-MID1013-Fw 5FAM
                                     (SEQ ID No: 18)
5'GGT CTG TCA TTA CCC AGT ATT C3'
```

Primer design, PCR reaction and thermocycling, capillary electrophoresis and fragment analysis are performed as for example 1.

Generally, two alleles can be present at DIP loci. One has a deletion of a few nucleotides. It corresponds to the short allele (S). The other allele has an insertion of a few nucleotides and corresponds to the long (L) allele. The STR loci represent portion of DNA having a pattern of two or more nucleotides that are tandemly repeated. Generally, the alleles' name correspond to the number of repetition of the pattern, for instance 3, 4, 5, 6, 7. Imagine that, at one locus, the S-DIP allele occurs next to the 4-STR allele, this forms the S4 haplotype. When the L-DIP and the 3-STR alleles are found together, this constitutes the L3 haplotype. The genotype of one individual heterozygous for these two haplotypes at this DIP-STR locus would be L3-S4. The advantage of the method we propose is that the determination of haplotypes is achieved with specific primers (FIG. 1). For the S-haplotypes, the 3' end of the specific primer (S-DIP primer) has to overlap the DIP locus sequence having the deletion (S-DIP allele). The other primer has to be located on the other side of the STR locus. For the L-haplotypes the principle is the same, except that the 3' end of the specific primer (L-DIP primer) has to be overlap the DIP locus sequence having the insertion (L-DIP allele).

Haplotype Frequencies

Two hundred six chromosomes from unrelated Swiss inhabitants having a Caucasian phenotype were genotyped for the three DIP-STR loci discussed above. Haplotype frequencies are indicated as percent in the following tables.

| Haplotype | % |
|---|---|
| MID1950-D20S473 | |
| 8S | 0.5 |
| 8L | 7.2 |
| 9L | 0.5 |
| 10S | 0.5 |
| 11S | 26.4 |
| 11L | 1.9 |
| 12S | 28.8 |
| 12L | 18.8 |
| 13S | 5.3 |
| 13L | 10.1 |
| MID1107-D5S1980 | |
| 13L | 47.1 |
| 14L | 4.9 |
| 15L | 5.9 |
| 16S | 0.5 |
| 17S | 0.5 |
| 17L | 10.8 |
| 18S | 0.5 |
| 19S | 20.1 |
| 19L | 1.0 |
| 20S | 5.4 |
| 21S | 2.9 |
| 22S | 0.5 |
| MID1013-D5S490 | |
| 11S | 0.5 |
| 12S | 0.5 |
| 13S | 3.4 |
| 14S | 69.4 |
| 15S | 3.4 |
| 15L | 1.5 |
| 16S | 0.5 |
| 20L | 5.3 |
| 21L | 2.9 |
| 22L | 1.5 |
| 23L | 7.3 |
| 24L | 1.9 |
| 25L | 0.5 |
| 26L | 1.0 |
| 27L | 0.5 |

Specificity Tests

Amplification specificity of the S-DIP and STR primers as well as L-DIP and STR primers was tested by amplifying increasing quantities of DNA template homozygous for the opposite DIP allele LL and SS respectively, regardless the genotype of the linked STR. The amount of DNA tested included four dilutions; ranging from 1 ng to 1000 ng. Amplifications were done in triplicate. For all three genetic markers tested, we found that the S-DIP and STR primers never amplified the LL DNA template, the same was true for the L-DIP and STR primers. Occasionally, we obtained spurious fragments due to the large amount of nonspecific template; however these fragments were outside the range of the expected amplicon size and couldn't be mistaken for an allele. These results suggest that the minor contributor of a DNA mixture should be detected even when it represents about 1‰ of the major contributor.

Sensitivity Tests

To examine the limit of DNA template required for successful amplification using S-DIP and STR primers as well as L-DIP and STR primers, we amplified seven dilutions of template DNA homozygous for the DIP allele SS and LL, respectively. The corresponding amounts of DNA were comprised between 250 pg to 3.9 pg. These tests were performed regardless the genotype of the linked STR. Amplifications were done in triplicate. We found that the detection threshold varies between 31.3 pg and 3.9 pg depending on the locus and haplotypes.

Casework Study

Background.

A case of a woman homicide investigated by DNA analysis is reported. Circumstantial evidences indicated three suspects, a man and his two sons.

Material

Three blood stains A, B, C were collected on the crime scene. Blood samples of the victim and the three suspects were available for comparison.

Methods

DNA was extracted using the QIAshredder and QIAamp kits (Qiagen AG Switzerland) according to the protocol of Castella et al. (2006) "Forensic evaluation of the QIAshredder/QIAamp DNA extraction procedure," Forensic Sci Int 156: 70-73. DNA profiling included standard fluorescent STR multiplex systems AmpFLSTR SGM Plus® (Applied Biosystems) and PowerPlex® Y (Promega) and 3 DIP-STR locus, MID1950-D20S473, MID1107-D5S1980 and MID1013-D5S490 as reported in the example section.

Results

DNA profiling of blood stains resulted in a complete AmpFLSTR SGM Plus® DNA profile matching the victim's profile and a complete PowerPlex® Y DNA profile matching the three related male suspects. These results are typically produced in the presence of a DNA mixture with a major fraction belonging to the victim and a minor fraction belonging to the perpetrator. The Y chromosome DNA profile indicated that all three suspects were potentially the source of the DNA but no exclusion of any of them was possible. In the effort of discriminating between the three suspects, we proceeded with the DIP-STR profiling.

The victim showed the genotypes MID1950-D20S473 12S-13S, MID1107-D5S1980 13L-14L and MID1013-D1S453 14S-14S (see table below). Being the victim homozygous for the S-, L- and S-DIP allele respectively, we genotyped the DNA from the blood stains A, B and C with the opposite S- or L-DIP and STR primers. DNA from stain A and C were 12L at MID1950-D20S473 and negative for the other markers. Sample B was always negative. We then compared these results to the DIP-STR genotypes of the three suspects (see table below). We found that at marker MID1013-D1S453 all suspect's genotypes still matched the blood stains DNA, at marker MID1107-D5S1980 only father and son$_1$ matched the blood stains DNA, and at marker MID1950-D20S473 only son$_1$ matched the blood stains DNA. Based on these DIP-STR results we could exclude son$_2$ and father as being at the origin of the blood stains, leaving only son$_1$ as the potential donor.

NB details of the trial background and complete genetic analyses are not reported here because of lack of relevance to the present scientific discussion.

| | DIP-STR | | | | | |
|---|---|---|---|---|---|---|
| | MID1950-D20S473 | | MID1107-D5S1980 | | MID1013-D5S490 | |
| | S | L | S | L | S | L |
| Victim | 12-13 | — | — | 13-14 | 14-14 | — |
| Blood stain A | nd | 12 | — | nd | nd | — |
| Blood stain B | nd | — | — | nd | nd | — |
| Blood stain C | nd | 12 | — | nd | nd | — |
| Father | 11-11 | — | — | 13-13 | 14-14 | — |
| Son$_1$ | 11 | 12 | — | 13-13 | 14-14 | — |
| Son$_2$ | 11-12 | — | 19 | 13 | 14-14 | — | nd: not determined

Example 4

Detection of Fetal DNA by DIP-STR Amplification of Maternal Plasma

Materials and Methods

Fetal DNA was extracted from maternal blood (10 mL) collected into a tube containing EDTA. To separate the plasma fraction, the blood sample was centrifugated at 1600×g for 10 min; the supernatant was transferred to a new tube and centrifugated again at 2800×g for 20 min. DNA was extracted from 2 mL of plasma using the QIAamp Blood Mini Kit (Qiagen), following the "Blood and Body Fluid Protocol" recommended by the manufacturer. Volumes of the used reagents were increased proportionately to accommodate the 2 mL sample size. Adsorbed DNA was eluted with 60 uL of water.

Saliva samples from the mother and the father were collected by cottonswabs and the DNA was extracted by QIAamp DNA Mini Kit (Qiagen) according to manufacturer's instructions. The PCR reaction was performed in a final volume of 20 μL containing 1×PCR buffer (Applied Biosystems) with 1.5 mM MgCl2, 125 μM of each dNTP, 1.2 U AmpliTaq Gold DNA Polymerase, 1 μM of each reverse (S-MID1950-Rev 5'AAA GAT GCT TTA TAT TTC CAG TTT AG3') and forward (D20S473-Fw NED5'TCA TGA GCT AAA TAT TAC TCA GTG C3') primers and 4 ng of genomic DNA or 10 uL of fetal DNA extracted as described above. Thermocycling conditions were: 3 min at 95° C.; followed by 60 sec at 94° C., 60 sec at 52° C. and 60 sec at 72° C. for 34 PCR-cycles, and a final extension of 30 min at 72° C. The thermal cyclers employed were GeneAmp 9700 (Applied Biosystems). Before capillary electrophoresis, 1 μL PCR product is added to 8.5 μL deionized formamide HI-DI (Applied Biosystems) and 0.5 μL GS-ROX 500 size standard (Applied Biosystems). DNA fragments were separated using an ABI PRISM 3100 Genetic Analyzer (Applied Biosystems) according to manufacturers' instruction and analyzed with GeneMapper ID v3.2 software (Applied Biosystems), with minimum interpretation peak threshold of 50 fluorescent units (RFU).

Results

Using one DIP-STR marker, MID 1950-D20S473, the presence of fetal DNA was detected in the peripheral blood of a pregnant woman at 30 weeks of amenorrhea. FIG. 2B shows the fetal DIP-STR haplotype transmitted from the father. The fetal origin of the haplotype is confirmed by the results of the DNA analysis of the father (FIG. 2 A) who shows the same haplotype transmitted to the son and by the results of the DNA analysis of the mother (FIG. 2 B) who doesn't have the detected DIP-STR haplotype.

The invention claimed is:

1. A method of detecting the presence of a DNA minor contributor in a DNA mixture by determining several haplotypes present in one or more DNA samples, each haplotype containing a short tandem repeat (STR) locus and a deletion insertion polymorphism (DIP) locus, comprising:
   i) determining the DIP genotype of the major DNA contributor in order to select suitable DIP primers for a specific amplification of the minor DNA contributor,
   ii) contacting said at least one or more DNA samples to be analyzed with a set of primers selected from the group consisting of a primer specific to the STR locus, a primer overlapping the short allele of the DIP locus (S-DIP), a primer overlapping the long allele of the DIP locus (L-DIP), and a combination of two or more of these primers,
   iii) amplifying the DNA mixture, for each DIP-STR locus, with the L-DIP and STR primers when the major contributor is SS, or with the S-DIP and STR primers when the major contributor is LL, wherein resulting amplicons, when present, correspond to the DIP-STR haplotype of the minor contributor,
   iv) evaluating the amplified amplicons in the DNA mixture to determine the haplotypes present at each of the loci analyzed in the set within the minor contributor and evaluating the match with the samples collected for comparison.

2. The method of claim 1, wherein the determination of the DIP genotype of the major DNA contributor in step i) comprises:
   contacting said one or more DNA samples or the DNA of the major contributor with primers which bind at each side of the DIP locus,
   amplifying the DIP locus and evaluating the amplicons, wherein the size of said amplicons is an indication of whether the deletion insertion polymorphism (DIP) locus is homozygous for the deletion (SS), homozygous for the insertion (LL) or heterozygous for both (SL).

3. The method of claim 1, wherein the distance between the STR locus and the DIP locus is smaller than 1000 base pairs.

4. The method of claim 1, wherein the set of primers of step ii) comprises a primer specific to the STR locus and a primer overlapping the short allele of the DIP locus (S-DIP).

5. The method of claim 1, wherein the set of primers of step ii) comprises a primer specific to the STR locus and a primer overlapping the long allele of the DIP locus (L-DIP).

6. The method of claim 1, wherein the DNA mixture of step iii) is amplified by polymerase chain reaction (PCR).

7. The method of claim 6, wherein the amplicons are separated using capillary or gel electrophoresis.

8. The method of claim 1, wherein the amplicons of step iv) are evaluated by comparing the amplicons to a size standard, wherein the size standard is selected from the group of size standards consisting of a DNA marker and a STR locus-specific allelic and DIP locus specific allelic ladders.

9. The method of claim 1, wherein the one or more DNA sample to be analyzed is selected from the group consisting of soft and hard tissues, blood, semen, epithelial or vaginal cells, hair, saliva, urine, feces, amniotic fluid containing placental cells or fetal cells, and mixtures of any of the tissues listed above.

10. A method of detecting the presence of a DNA minor contributor in a DNA mixture by determining several haplotypes present in one or more DNA samples, each haplotype containing a short tandem repeat (STR) locus and a deletion insertion polymorphism (DIP) locus, comprising:
    i) contacting said at least one or more DNA mixtures and/or DNA samples to be analyzed with a combination of two or more sets of primers selected from the group consisting of a primer specific to the STR locus, a primer overlapping the short allele of the DIP locus (S-DIP), and a primer overlapping the long allele of the DIP locus (L-DIP),
    ii) amplifying said at least one or more DNA mixtures and/or DNA samples, wherein resulting amplicons, when present, correspond to the DIP-STR haplotypes of the minor contributor, and of the major contributor,
    iii) evaluating the amplified amplicons in the DNA mixture and/or DNA sample to determine the haplotypes present at each of the loci analyzed in said at least one or more DNA mixtures and/or DNA samples and evaluating the match between said at least two or more DNA mixtures and/or DNA samples for comparison.

11. The method of claim 10, wherein the distance between the STR locus and the DIP locus is smaller than 1000 base pairs.

12. The method of claim 10, wherein the DNA mixture of step ii) is amplified by polymerase chain reaction (PCR).

13. The method of claim 12, wherein the amplicons are separated using capillary or gel electrophoresis.

14. The method of claim 10, wherein the amplicons of step iii) are evaluated by comparing the amplicons to a size standard, wherein the size standard is selected from the group of size standards consisting of a DNA marker and a STR locus-specific allelic and DIP locus specific allelic ladders.

15. The method of claim 10, wherein the one or more DNA mixtures to be analyzed is selected from the group comprising soft and hard tissues, blood, semen, epithelial or vaginal cells, hair, saliva, urine, feces, amniotic fluid containing placental cells or fetal cells, and mixtures of any of the tissues listed above.

16. A method of detecting the presence of a DNA minor contributor in a DNA mixture by determining several haplotypes present in one or more DNA samples, each haplotype containing a short tandem repeat (STR) locus and a deletion insertion polymorphism (DIP) locus, comprising:
  i) determining the DIP genotype of the major DNA contributor in order to select suitable DIP primers for a specific amplification of the minor DNA contributor,
  ii) contacting said at least one or more DNA samples to be analyzed with a set of primers selected from the group consisting of a primer specific to the STR locus, a primer overlapping the short allele of the DIP locus (S-DIP), a primer overlapping the long allele of the DIP locus (L-DIP), and a combination of two or more of these primers,
  iii) amplifying the DNA mixture, for each DIP-STR locus, with the L-DIP, S-blocking primer and STR primers when the major contributor is SS, or with the S-DIP, L-blocking primer and STR primers when the major contributor is LL, wherein resulting amplicons, when present, correspond to the DIP-STR haplotype of the minor contributor,
  iv) evaluating the amplified amplicons in the DNA mixture to determine the haplotypes present at each of the loci analyzed in the set within the minor contributor and evaluating the match with the samples collected for comparison.

17. The method of claim 16, wherein the determination of the DIP genotype of the major DNA contributor in step i) comprises:
  contacting said one or more DNA samples or the DNA of the major contributor with primers which bind at each side of the DIP locus,
  amplifying the DIP locus and evaluating the amplicons, wherein the size of said amplicons is an indication of whether the deletion insertion polymorphism (DIP) locus is homozygous for the deletion (SS), homozygous for the insertion (LL) or heterozygous for both (SL).

18. The method of claim 16, wherein the distance between the STR locus and the DIP locus is smaller than 1000 base pairs.

19. The method of claim 16, wherein the set of primers of step ii) comprises a primer specific to the STR locus and a primer overlapping the short allele of the DIP locus (S-DIP).

20. The method of claim 16, wherein the set of primers of step ii) comprises a primer specific to the STR locus and a primer overlapping the long allele of the DIP locus (L-DIP).

21. The method of claim 16, wherein the DNA mixture of step iii) is amplified by polymerase chain reaction (PCR).

22. The method of claim 21, wherein the amplicons are separated using capillary or gel electrophoresis.

23. The method of claim 16, wherein the amplicons of step iv) are evaluated by comparing the amplicons to a size standard, wherein the size standard is selected from the group of size standards consisting of a DNA marker and a STR locus-specific allelic and DIP locus specific allelic ladders.

24. The method of claim 16, wherein the one or more DNA sample to be analyzed is selected from the group consisting of soft and hard tissues, blood, semen, epithelial or vaginal cells, hair, saliva, urine, feces, amniotic fluid containing placental cells or fetal cells, and mixtures of any of the tissues listed above.

* * * * *